(12) United States Patent
Balgobin et al.

(10) Patent No.: US 8,795,316 B2
(45) Date of Patent: *Aug. 5, 2014

(54) IMPLANTABLE MEDICAL DEVICE DELIVERY SYSTEM WITH A FRANGIBLE PORTION AND METHODS OF MAKING AND USING THE SAME

(75) Inventors: Keith Balgobin, Pembroke Pines, FL (US); Vladimir Mitelberg, Austin, TX (US); John H. Thinnes, Jr., Miami Beach, FL (US)

(73) Assignee: DePuy Syntheses Products, LLC, Raynham, MA (US)

( * ) Notice: Subject to any disclaimer, the term of this patent is extended or adjusted under 35 U.S.C. 154(b) by 1051 days.

This patent is subject to a terminal disclaimer.

(21) Appl. No.: 11/739,744

(22) Filed: Apr. 25, 2007

(65) Prior Publication Data

US 2008/0269719 A1 Oct. 30, 2008

(51) Int. Cl.
*A61M 29/00* (2006.01)
*A61B 17/12* (2006.01)

(52) U.S. Cl.
CPC ..... *A61B 17/12027* (2013.01); *A61B 17/12113* (2013.01); *A61B 2017/12054* (2013.01)
USPC ........................................................ 606/200

(58) Field of Classification Search
CPC .......................... A61B 2017/1205–2017/12054
USPC ................................. 606/108, 200; 623/1.11
See application file for complete search history.

(56) References Cited

U.S. PATENT DOCUMENTS

| | | | |
|---|---|---|---|
| 3,476,115 A | 11/1969 | Graeff et al. | |
| 4,973,312 A | 11/1990 | Andrew | |
| 5,108,407 A | 4/1992 | Geremia et al. | |
| 5,250,071 A * | 10/1993 | Palermo | 606/198 |
| 5,284,485 A | 2/1994 | Kammerer et al. | |
| 5,330,491 A * | 7/1994 | Walker et al. | 606/148 |
| 5,334,199 A | 8/1994 | Yoon | |
| 5,403,331 A | 4/1995 | Cheserfield et al. | |

(Continued)

FOREIGN PATENT DOCUMENTS

| | | |
|---|---|---|
| EP | 0 778 040 | 6/1997 |
| EP | 0 935 947 | 8/1999 |

(Continued)

OTHER PUBLICATIONS

U.S. Appl. No. 11/461,231, Mitelberg et al.

(Continued)

*Primary Examiner* — Darwin Erezo
*Assistant Examiner* — Jonathan Hollm
(74) *Attorney, Agent, or Firm* — Cook Alex Ltd.

(57) ABSTRACT

An implantable medical device delivery system is provided with a carrier member having a proximal portion, a distal portion, and a frangible portion intermediate the proximal and distal portions. The frangible portion includes at least one notch providing a break hinge. A locking member is fixedly secured to the proximal portion of the carrier member and is releasably connected to an implantable medical device at or adjacent to the distal portion of the carrier member. In use, the implantable medical device is positioned generally adjacent to a target location of a body vessel and the frangible portion is broken about the break hinge. The proximal portion of the carrier member is then moved away from the distal portion to retract the locking member, thereby deploying the implantable medical device.

10 Claims, 4 Drawing Sheets

(56) References Cited

U.S. PATENT DOCUMENTS

| | | | |
|---|---|---|---|
| 5,601,600 A * | 2/1997 | Ton | 606/206 |
| 5,690,649 A | 11/1997 | Li | |
| 5,989,242 A | 11/1999 | Saadat et al. | |
| 6,277,126 B1 * | 8/2001 | Barry et al. | 606/108 |
| 6,346,091 B1 * | 2/2002 | Jacobsen et al. | 604/57 |
| 6,428,558 B1 * | 8/2002 | Jones et al. | 606/200 |
| 6,478,773 B1 | 11/2002 | Gandhi et al. | |
| 6,793,673 B2 * | 9/2004 | Kowalsky et al. | 623/2.36 |
| 6,835,185 B2 * | 12/2004 | Ramzipoor et al. | 604/57 |
| 7,819,892 B2 * | 10/2010 | Balgobin et al. | 606/200 |
| 7,985,238 B2 * | 7/2011 | Balgobin et al. | 606/200 |
| 2006/0276823 A1 * | 12/2006 | Mitelberg et al. | 606/200 |
| 2006/0276824 A1 * | 12/2006 | Mitelberg et al. | 606/200 |
| 2006/0276825 A1 * | 12/2006 | Mitelberg et al. | 606/200 |
| 2006/0276826 A1 * | 12/2006 | Mitelberg et al. | 606/200 |
| 2006/0276827 A1 * | 12/2006 | Mitelberg et al. | 606/200 |
| 2006/0276828 A1 * | 12/2006 | Balgobin et al. | 606/200 |
| 2006/0276829 A1 * | 12/2006 | Balgobin et al. | 606/200 |
| 2006/0276830 A1 * | 12/2006 | Balgobin et al. | 606/200 |
| 2006/0276832 A1 * | 12/2006 | Balgobin et al. | 606/200 |
| 2006/0276833 A1 * | 12/2006 | Balgobin et al. | 606/200 |
| 2006/0276834 A1 * | 12/2006 | Balgobin et al. | 606/200 |
| 2007/0010849 A1 | 1/2007 | Balgobin et al. | |
| 2007/0010850 A1 * | 1/2007 | Balgobin et al. | 606/200 |
| 2008/0300616 A1 * | 12/2008 | Que et al. | 606/191 |

FOREIGN PATENT DOCUMENTS

| | | |
|---|---|---|
| EP | 1 738 698 | 1/2007 |
| WO | WO 93/21830 | 11/1993 |
| WO | WO 2007/070797 | 6/2007 |

OTHER PUBLICATIONS

U.S. Appl. No. 11/461,245, Mitleberg et al.

Extended European Search Report dated May 6, 2009, in European Patent Application No. 08251336.7.

* cited by examiner

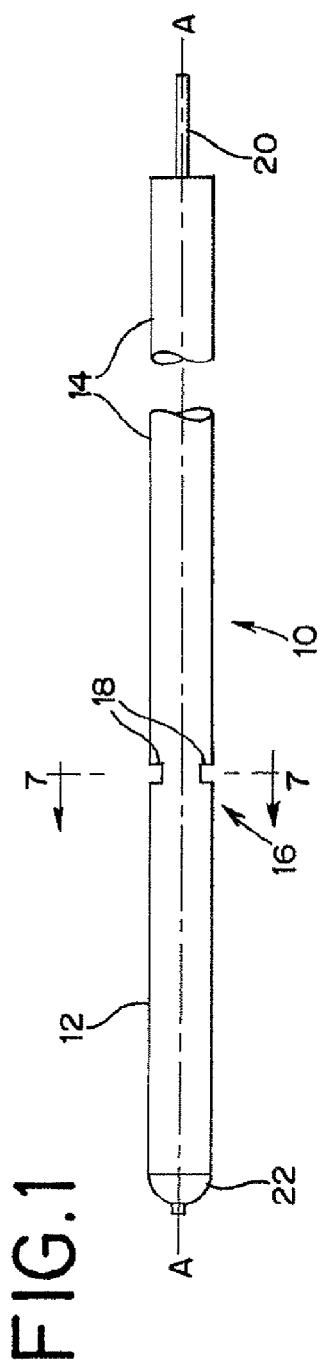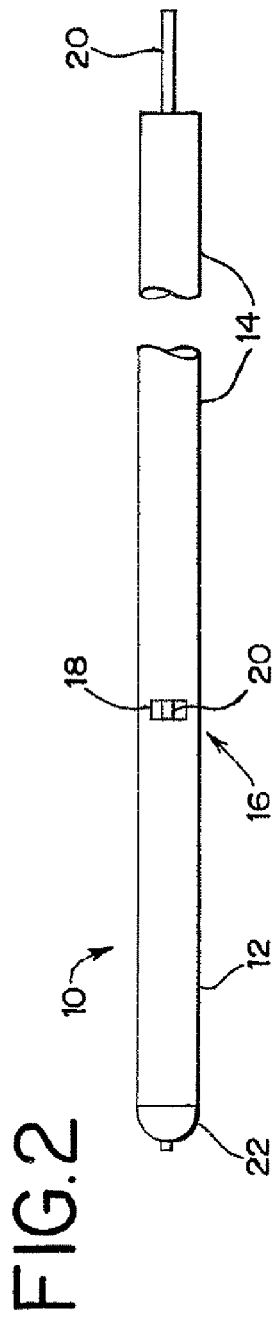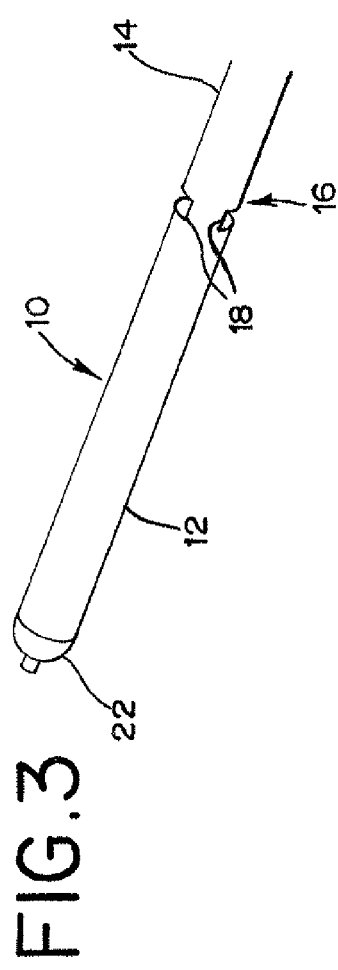
FIG.1
FIG.2
FIG.3

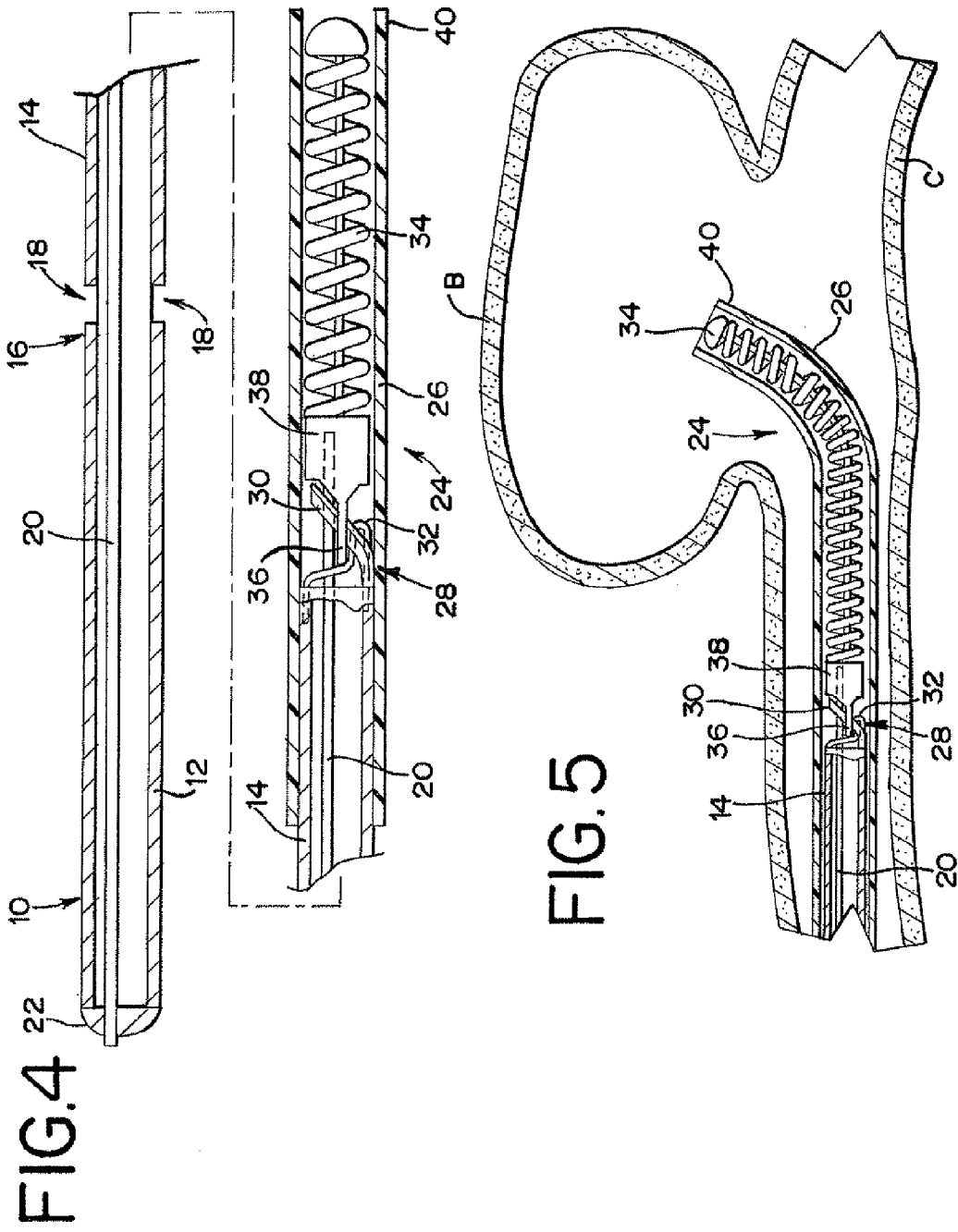

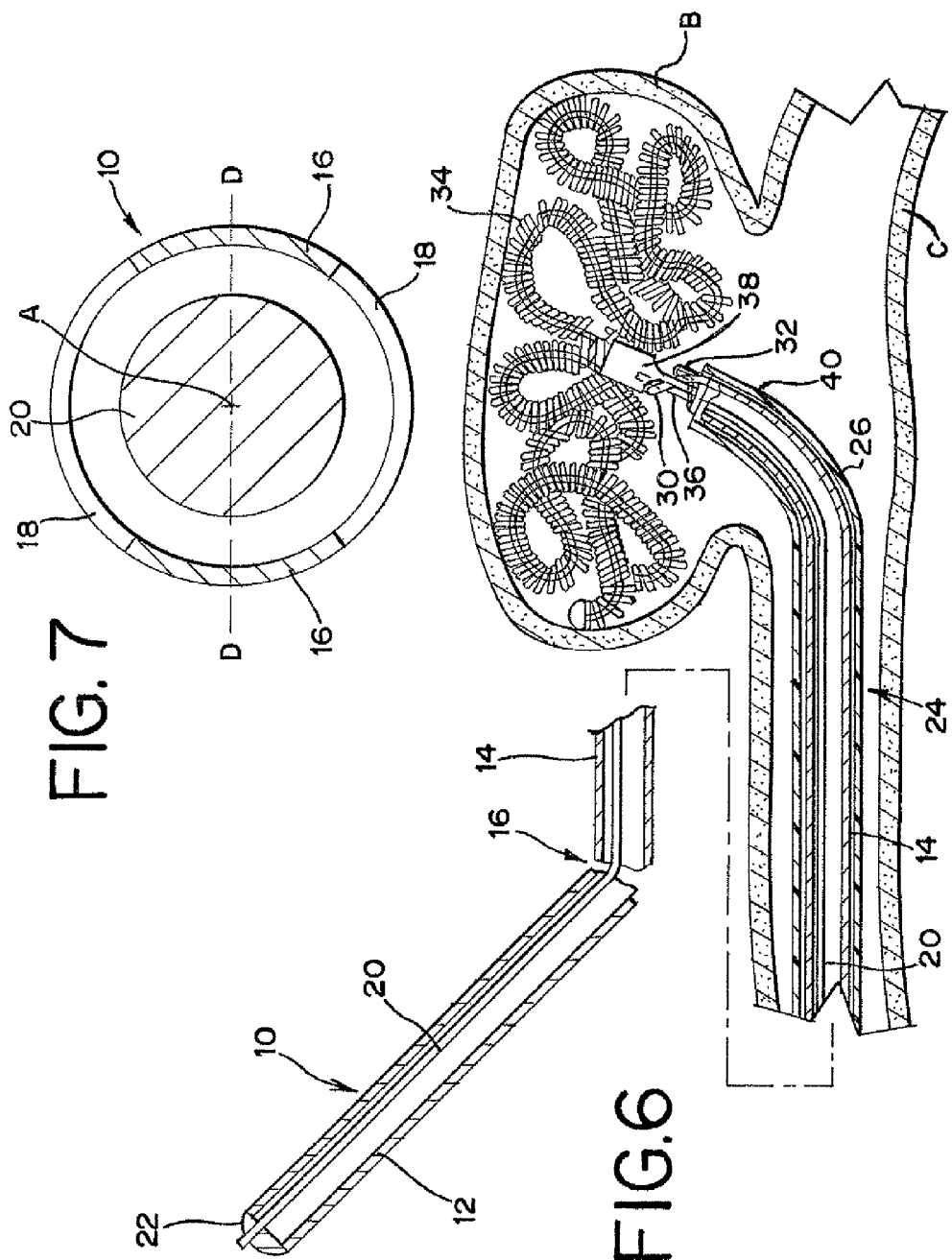

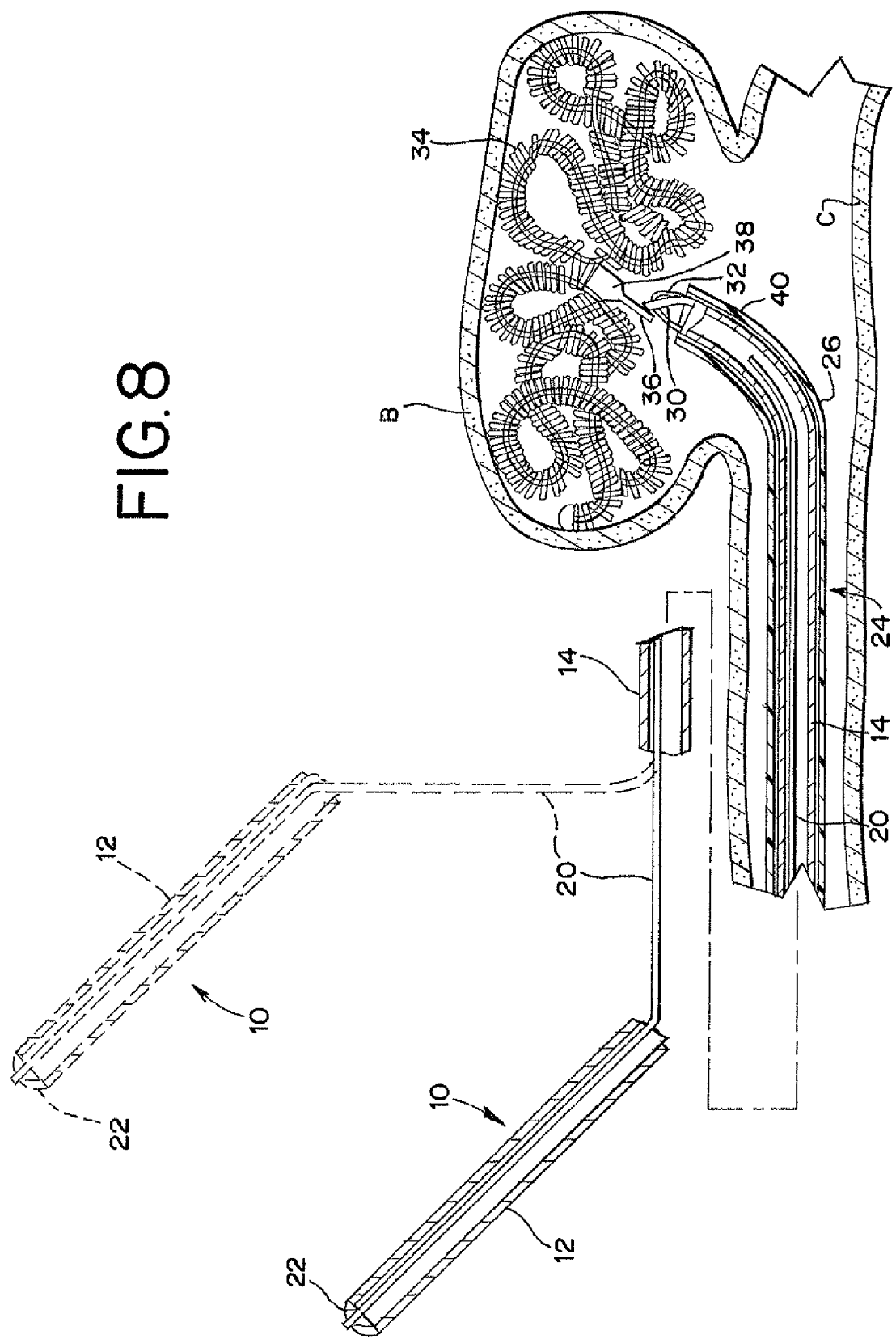

IMPLANTABLE MEDICAL DEVICE DELIVERY SYSTEM WITH A FRANGIBLE PORTION AND METHODS OF MAKING AND USING THE SAME

FIELD OF THE INVENTION

This invention generally relates to interventional medical device systems that are navigable through body vessels of a human subject. More particularly, this invention relates to delivery systems for deploying an implantable medical device to a target location of a body vessel and methods of manufacturing and using the same.

DESCRIPTION OF RELATED ART

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery location. A vascular occlusion device, such as an embolic coil, is attached to the end of a delivery member which pushes the coil through the catheter and out of the distal end of the catheter into the delivery location. Some of the problems that have been associated with these procedures relate to the accuracy of coil placement. For example, the coil detachment mechanism may cause the embolic coil to partially or fully dislodge from the predetermined location or dislodge previously deployed coils.

In response to accuracy concerns, numerous devices and release mechanisms have been developed in an attempt to provide a deployment system which allows control of the occlusion device after the device has been delivered by the catheter and to also provide a rapid release or detachment mechanism to release the device once it is in place. One such detachment system is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that have the potential to interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

The above-identified delivery systems typically require electronic equipment powered by a power source and if the electronic equipment is defective or the power source fails, the procedure may be prolonged while the equipment is repaired or replaced. Prolonging the procedure may expose the patient to additional risk.

To avoid the problems associated with such heat- and/or electricity-based detachment systems, numerous mechanical deployment systems have been proposed. For example, U.S. Pat. No. 5,250,071 to Palermo, which is hereby incorporated herein by reference, describes a detachment system whereby interlocking clasps of the system and the coil are held together by a control wire. The control wire is moved proximally to disengage the clasps from each other.

While this and similar delivery and detachment systems avoid the need for electronic equipment, many require a separate handle component, such as an attachable handle, a peelable sheath system, and/or a syringe, which is manipulated by the medical professional to release the implantable device. Attachable handle components often require the use of additional components, such as a re-zip sheath, for proper operation with a system including a catheter or introducer component. This tends to increase the time and complexity of releasing the implantable device, as well as increasing the component and packaging costs.

Mechanical delivery and detachment systems avoiding the need for an attachable handle and a re-zip sheath are described in U.S. patent application Ser. Nos. 11/461,231 and 11/461,245 to Mitelberg et al., filed Jul. 31, 2006, both of which are hereby incorporated herein by reference. Delivery and detachment systems of U.S. patent application Ser. No. 11/461,245 are provided with a hypotube having a distal end and a locking member associated with the distal end. The hypotube also has a proximal end separated from the distal end by a spiral-cut portion. The spiral-cut portion is axially movable from a compressed condition to an elongated condition. In one embodiment, the locking member is a wire adapted to engage an implantable medical device when the spiral-cut portion is in the compressed condition. The wire is anchored to the proximal portion of the hypotube, such that movement of the spiral-cut portion from the compressed condition to the elongated condition retracts the wire and causes it to separate from the implantable device, thereby deploying the device to a target location of a body vessel.

Delivery and detachment systems according to U.S. patent application Ser. No. 11/461,231 employ a variation of the deployment system of U.S. patent application Ser. No. 11/461,245. In such systems, selected turns of the spiral-cut portion of the hypotube are joined to adjacent turns by frangible bridge members. As the spiral-cut portion is elongated, the bridge members must be broken to fully elongate the spiral-cut portion and retract the locking wire.

The delivery and detachment systems of U.S. patent application Ser. Nos. 11/461,231 and 11/461,245 overcome the above-referenced problems of other known systems, but require the creation of a spiral-cut portion, typically by a laser-cutting operation, during manufacture. Implementation of a spiral-cut portion may increase the difficulty and/or duration of the manufacturing process, so there remains the need for an implantable medical device delivery system incorporating a simplified detachment system.

SUMMARY

In accordance with one embodiment or aspect of the present invention, a delivery system for delivering an implantable medical device to a target location of a body vessel is provided with a generally hollow tubular carrier member defining a longitudinal axis and having a proximal portion, a distal portion, and a frangible portion intermediate said proximal portion and said distal portion. The frangible portion has at least one notch which provides a break hinge transverse to the longitudinal axis of the carrier member. The frangible portion has a breaking strength about the break hinge which is less than a breaking strength about any other line transverse to the longitudinal axis of the carrier member. The delivery device also includes a locking member at least partially received within the carrier member. The locking member extends at least from the proximal portion of the carrier member to the distal portion of the carrier member and is fixedly secured to the proximal portion. The locking member is adapted to be releasably connected to an implantable medical device.

According to another embodiment or aspect of the present invention, a method is provided for manufacturing a delivery system for delivering an implantable medical device to a target location of a body vessel. The method includes providing a generally hollow tubular carrier member having a proximal portion and a distal portion and defining a longitudinal axis. At least one notch is formed in the carrier member intermediate the proximal portion and the distal portion, which notch provides a break hinge transverse to the longitudinal axis. The carrier member has a breaking strength about the break hinge which is less than a breaking strength about any other line transverse to the longitudinal axis. The delivery system is also provided with a locking member at least partially received within the carrier member and extending at least from the proximal portion of the carrier member to the distal portion of the carrier member. A portion of the locking member is fixedly secured to the proximal portion of the carrier member.

According to yet another embodiment or aspect of the present invention, a method is provided for deploying an implantable medical device to a target location of a body vessel. The method includes providing a delivery system having a generally hollow tubular carrier member, a locking member, and an implantable medical device. The carrier member defines a longitudinal axis and has a distal portion, a proximal portion, and a frangible portion intermediate the distal portion and the proximal portion. The locking member is at least partially received within the carrier member, extending at least from the proximal portion of the carrier member to the distal portion of the carrier member, and has a portion fixedly secured to the proximal portion of the carrier member. The implantable medical device is releasably connected to the locking member at or adjacent to the distal portion of the carrier member. In use, the implantable medical device is positioned generally adjacent to a target location of a body vessel and then the carrier member is broken at the frangible portion along a break hinge transverse to the longitudinal axis. The breaking strength about the break hinge is less than a breaking strength about any other line transverse to the longitudinal axis. The proximal portion of the carrier member is then moved away from the distal portion of the carrier member to retract the locking member, thereby disengaging the locking member from the implantable medical device.

Special application for the present invention has been found for deploying embolic coils to aneurysms in the neurovascular system. However, the present invention is also applicable to the deployment of other devices, including stents, to other portions of the vascular system, so it will be understood that the products and methods described herein are not limited to particular medical devices or particular surgical applications.

BRIEF DESCRIPTION OF THE DRAWINGS

FIG. 1 is a side elevational view of a carrier member having a frangible portion with two notches according to an aspect of the present invention;

FIG. 2 is a top plan view of the carrier member of FIG. 1;

FIG. 3 is a front perspective view of the carrier member of FIG. 1;

FIG. 4 is a partial cross-sectional view of an implantable medical device delivery system incorporating the carrier member of FIG. 1;

FIG. 5 is a partial cross-sectional view of a distal portion of the delivery system of FIG. 4 in a body vessel;

FIG. 6 is a partial cross-sectional view of the delivery system of FIG. 5, with the frangible portion of the carrier member in a broken condition and the medical device positioned for deployment within an aneurysm;

FIG. 7 is a cross-sectional view of the frangible portion of a carrier member according to the present invention, taken through the line 7-7 of FIG. 1; and FIG. 8 is a partial cross-sectional view of the delivery system of FIG. 6, with a proximal portion of the carrier member moved away from a distal portion of the carrier member to release the medical device from the delivery system.

DESCRIPTION OF ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1-3 illustrate a generally hollow tubular structure or carrier member 10 suitable for incorporation into an implantable medical device delivery system according to an aspect of the present invention. When used herein, the terms "tubular" and "tube" are to be construed broadly and are not limited to a structure that is a right cylinder or strictly circumferential in cross-section or of a uniform cross-section throughout its length. For example, the carrier member 10 is shown as a substantially right cylindrical structure, but may have a tapered or curved outer surface without departing from the scope of the present invention.

The carrier member 10 defines a longitudinal axis "A" and has a proximal portion 12, a distal portion 14, and a frangible portion 16 intermediate the proximal portion 12 and the distal portion 14. In one embodiment, the carrier member 10 may be a hypotube comprised of a biocompatible metallic material, such as stainless steel. The hypotube typically will have a diameter of between about 0.008 to about 0.020 inch, at times between about 0.010 inch and about 0.015 inch, an example of a specific tube diameter being approximately 0.013 inch. Such a carrier member is suitable for delivering and deploying embolic coils to target locations, typically aneurysms, within the neurovasculature, but differently sized carrier members comprised of other materials may be useful for different applications and are within the scope of the present invention.

The frangible portion 16 comprises at least one open window or notch 18, preferably passing entirely through the wall of the carrier member 10. In the illustrated embodiment of FIGS. 1-3, the frangible portion 16 comprises two notches 18 which are substantially identical to each other and in facing relationship to each other. Other configurations of the frangible portion 16 are also within the scope of the present invention, such as configurations incorporating a single notch, two or more differently shaped notches, or notches defined by one or more curved walls. The notches 18 weaken the frangible portion 16 compared to the remainder of the carrier member 10, and are useful for deploying an implantable medical device, as will be described in greater detail herein.

According to one method of manufacturing the carrier member 10, a generally hollow tubular member and a cutting device (not illustrated) are provided. The nature of the cutting device depends on the material of the tubular member, but a laser is a suitable cutting device for use with a metallic tubular member. In the case of a stainless steel tubular member suitable for use in delivering a neurovascular implant, i.e. a tubular member having an outer diameter no greater than 0.025 inch, the laser may be adapted to provide a kerf in the range of about 0.005 inch to about 0.015 inch (a specific example being 0.010 inch). The notches 18 are formed by cutting openings into the frangible portion 16.

When using a laser, the notches may be formed one or two at a time. To form a single notch, the laser may be applied to the frangible portion along a line generally tangential to the wall of the tubular member. To form two notches in a single carrier member, a pair of tangentially directed lasers may be employed, with each laser separately forming one notch. In yet another embodiment, a single laser may be applied to the frangible portion along a line generally transverse to and through the longitudinal axis of the tubular member. The laser will cut through the wall of the tubular member to define a first notch, pass through the hollow interior, and cut through the wall on the other side of the tubular member to define a second notch in facing relationship to the first notch. If the notch is to be larger than the opening defined by the laser, the laser and/or the tubular member may be moved relative to the other while continuing to operate the laser to fully define the notch.

While cutting, and particularly laser-cutting, is one method of forming notches in the carrier member, other methods may be also employed. For example, the notches may be formed by chemical etching or the like without departing from the scope of the present invention.

The delivery system further includes an elongated locking member 20. The locking member 20 may take any of a number of forms including, but not limited to a tube or a wire having a circular or other cross-section. The locking member 20 is at least partially received within the carrier member 10 and fixedly secured to the proximal portion 12. In the embodiment of FIGS. 1-3, the locking member 20 is illustrated as an actuation wire which is secured to a plug 22 that forms the proximal end of the proximal portion 12. While the locking member 20 is shown as being fixed at the proximal end of the carrier member 10, it may be secured at any area(s) of the proximal portion 12 without departing from the scope of the present invention. The locking member 20 may be comprised of any of a number of materials, typically a metallic material or a polymeric material, and the method of securing the locking member 20 to the proximal portion 12 may vary depending on the material composition of each structure. For example, a number of known methods which may be suitable include, but are not limited to adhesion, welding, soldering, crimping, and swaging.

The locking member 20 extends at least from the proximal portion 12 to the distal portion 14 of the carrier member 10. In contrast to the proximal portion 12, the distal portion 14 is not fixedly secured to the locking member 20. Instead, the area of the locking member 20 passing through the distal portion 14 of the carrier member 10 is adapted to be releasably connected to an implantable medical device, such as an embolic coil. As used herein, the phrase "releasably connected" refers to the implantable medical device being temporarily held at or adjacent to the distal portion 14 of the carrier member 10 at least in part by operation of the locking member 20 and being released by manipulation of the locking member 20. Hence, a locking member 20 may be "releasably connected to an implantable medical device" without physically contacting the device, for example, in the case of a locking member that directly engages a detachment mechanism which, in turn, contacts and holds the implantable medical device.

In some embodiments, the locking member 20 may extend beyond the distal end of the distal portion 14, which may be advantageous for engagement with an implantable medical device held adjacent to and outside of the distal portion 14 of the carrier member 10, as shown in FIG. 4 and as will be described in greater detail herein. The locking member 20 may be incorporated into the carrier member 10 before or after the notches 18 are formed, but it may be preferred to apply the notches first to avoid possibly damaging the locking member with a laser or other forming device used to form the notches.

FIG. 4 shows one embodiment of a fully configured delivery system 24, in partial cross-section and in a pre-deployment condition. In addition to the carrier member 10 and locking member 20, the illustrated delivery system 24 further includes a tubular catheter or introducer 26 and a detachment mechanism generally designated at 28. The introducer 26 may be provided according to known design, sized and configured to be movable through a body vessel and having a lumen adapted to receive at least a portion of the carrier member 10. It will be seen that a carrier member 10 according to the present invention does not require an attachable handler so it may be used with the introducer 26 without the need for a re-zip sheath. This saves time and reduces complications for physicians and reduces system component costs.

The detachment mechanism 28 may take any of a number of configurations, provided that it is adapted to cooperate with the locking member 20 to release an implantable medical device when the locking member 20 is retracted. The illustrated detachment mechanism 28 is associated with the distal portion 14 of the carrier member 10, has an engagement member 30 and a kicker member 32, and conforms generally to the system described in U.S. Patent Application Publication No. US 2007/0010849 to Balgobin et al., which is hereby incorporated herein by reference. The operation of the illustrated detachment mechanism 28 will be described in greater detail herein.

The implantable medical device 34 illustrated in FIG. 4 is an embolic coil. However, it will be appreciated that virtually any implantable medical device may be delivered and deployed by delivery systems according to the present invention.

To connect the implantable medical device 34, a portion of the engagement member 30 of the detachment mechanism 28 is passed through an aperture 36 at a proximal end 38 of the implantable medical device 34. Passing the engagement member 30 through the aperture 36 causes the aperture 36 to contact the kicker member 32 and deform the kicker member 32 (which is U-shaped at rest, as shown in FIG. 8) to the illustrated condition. The kicker member 32 may be resilient, such that when so deformed it provides a force sufficient to unseat the aperture 36 from the engagement member 30. The implantable medical device 34 is finally locked onto the detachment mechanism 28 by passing a portion of the locking member 20 through an opening of the engagement member 30, as shown in FIG. 4. Hence, it will be seen that retracting the locking member 20 will allow the kicker member 32 to return to its original configuration, thereby separating the implantable medical device 34 from the delivery system 24.

Regardless of the means employed to secure the implantable medical device 34, a device thus engaged may be delivered to a target location "B" within a body vessel "C" by the introducer 26 (FIG. 5). According to one method of delivering the device 34, the introducer 26 is fed through the vasculature until a distal end 40 thereof is adjacent to the target location "B." Thereafter, the distal portion 14 of the carrier member 10 and the associated implantable medical device 34 are advanced through the lumen of the introducer 26 until the device 34 is itself generally adjacent to the target location "B." Alternatively, part of the distal portion 14 of the carrier member 10 and the associated device 34 may be pre-loaded in the introducer 26, with the combination being fed through the vasculature to the target location "B." Other methods of positioning the implantable medical device 34 generally adjacent to a target location of a body may also be practiced without departing from the scope of the present invention.

To more accurately position the engaged device, radiopaque markers (not illustrated) may be attached to the carrier member or the device itself.

When the engaged device 34 has been properly positioned and oriented, it is disengaged from the detachment mechanism 2B by retracting the locking member 20. This is initiated by breaking the carrier member 10 at the frangible portion 16, which remains outside of the body of the patient and proximal of the introducer 26, as shown in FIG. 6. Preferably, the frangible portion 16 is broken by applying a human digital breaking force generally transverse to the longitudinal axis "A" of the carrier member 10, in the direction of a notch 18 or in the opposite direction. In the embodiment of FIG. 6, one notch is facing upwardly and the other is facing downwardly (also shown in FIG. 4), so a breaking force may be applied either upwardly or downwardly. FIG. 6 shows the result of a breaking force applied by holding the distal portion 14 of the carrier member 10 stationary and pressing the proximal portion 12 upwardly such as by grasping same and bending the proximal portion 12 and break the frangible portion 16.

A frangible portion 16 with two notches 18 in facing relationship to each other may be an advantageous configuration because it provides a "bi-directional" break hinge "D," as shown in the cross-sectional view of FIG. 7. It will be appreciated by those of ordinary skill in that art that the absence of carrier member material at the notches 18 makes them weaker than the remainder of the carrier member 10. When a breaking force is applied according to the foregoing description, the proximal portion 12 bends upwardly about the break hinge "D" until the frangible portion 16 breaks at the notches 18. If a break force is applied to the proximal portion 12 in the opposite direction, the proximal portion 12 will bend downwardly about the break hinge "D" until the frangible portion 16 breaks. When the two notches 18 are substantially identical and arranged in a facing relationship to each other, as in FIG. 7, the breaking force required to break the frangible portion 16 will be substantially the same whether it is applied upwardly or downwardly, which makes the break hinge "D" "bi-directional." If there is only one notch, the break hinge will be "uni-directional" in that the breaking strength will be different depending on whether the breaking force is applied in the direction of the notch or in the opposite direction.

The notches 18 are areas of decreased breaking strength, so the breaking strength of the frangible portion 16 is less about a "bi-directional" or "uni-directional" break hinge "D" than about any other line in the plane of the notches. For example, it would require a much greater breaking force to break the frangible portion 16 about a vertical line in the plane of the notches 18 (by holding the distal portion 14 stationary and pressing the proximal portion 12 to the left or right) because the material between the notches 18 provides for increased breaking strength.

The magnitude of the breaking force required to break the frangible portion 16 about the break hinge "D" depends in part on the size of the notch 18. In general, the required breaking force will decrease with a larger notch and increase with a smaller notch. Thus, the minimum breaking strength of the frangible portion 16 may be controlled by controlling the width (i.e., the arcuate extent) and the length (i.e., the dimension amount in the direction of the longitudinal axis "A") of the notch 18. In one embodiment, the frangible portion 16 is adapted such that it will not break until a sufficient breaking force is applied. Such an embodiment functions as a safety mechanism, because the implantable medical device 34 cannot be released until a minimum breaking force is applied by the medical professional.

As described previously, the breaking force may be applied by holding the distal portion 14 stationary and pressing the proximal portion 12, but there are many other ways of applying a breaking force. For example, a breaking force may be applied by holding the proximal portion 12 stationary and pressing on the distal portion 14 or by moving the proximal portion 12 and distal portion 14 in opposite directions to create a shear force at the frangible portion 16. Hence, those of ordinary skill in the art will appreciate that there are a number of ways to apply a breaking force, and the present invention is not limited to a particular method of applying a breaking force.

When the frangible portion 16 has been broken, the proximal portion 12 of the carrier member 10 is moved away from the distal portion 14, as shown in FIG. 8. The proximal portion 12 may be moved along a path parallel to the longitudinal axis "A" of the carrier member 10, as shown in solid lines, or along a path at an angle to the longitudinal axis "A," as shown in broken lines. The locking member 20 is fixedly secured to the proximal portion 12, so this movement will retract the locking member 20. After sufficient retraction of the locking member 20, it will disengage the implantable medical device 34 and the detachment mechanism 28, which allows the kicker member 32 to return to a U-shaped condition, thereby deploying the implantable medical device 34 to the target location "B." Thereafter, the introducer 26 and the delivery system 24 are removed from the vasculature.

The foregoing description illustrates one method of using a delivery device according to the present invention, but other methods may also be used without departing from the scope of the present invention.

It will be seen from the preceding description that delivery systems according to the present invention eliminate numerous problems associated with known devices. In particular, delivery systems and associated methods of use according to the present invention ensure that the implantable device is completely separated from the engagement system and deployed to the target location. Further delivery systems according to the present invention may be manufactured in a simple, low-cost manner and do not require additional components, such as an attachable handle or re-zip sheath.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A delivery system for delivering an implantable medical device, to a target location of a body vessel, comprising:
    a generally hollow tubular carrier member having a lumen and a circumference defining a longitudinal axis and having a wall thickness, the carrier member having:
        a proximal portion, which is adapted to remain outside the body when in use;
        a distal portion, at least a portion of which is adapted to be positioned inside the body when in use;
        a frangible portion intermediate said proximal portion and said distal portion and positioned to remain outside of the body vessel during delivery of the implantable medical device, wherein said frangible portion comprises two notches in facing relationship to each other, each notch passes entirely through the wall thickness along an arcuate extent less than half the circumference, said frangible portion being a bi-directional break hinge in the direction of either said notch and transverse to said longitudinal axis of the carrier member, and wherein the frangible portion has a breaking strength about said break hinge less than a breaking strength about any other line transverse to said longitudinal axis of the carrier member, whereby the frangible portion breaks by applying a human digital breaking force generally transverse to said longitudinal axis to provide a separated carrier member proximal portion;
    an implantable medical device;
    a locking member that is a tube or wire at least partially received within the carrier member lumen, extending axially within the lumen at least from the proximal portion of the carrier member to the distal portion of the carrier member, and adapted to be mechanically and releasably connected to the implantable medical device;
    the implantable medical device having a proximal end that has a proximally extending member with a first face and a second face, said faces being oppositely facing, the proximally extending member having an aperture through same and through its first and second faces;
    the first and second faces of the proximally extending member each being spaced away from the tubular carrier lumen, thereby defining a first open space between the first face and the lumen as well as a second open space between the second face and the lumen;
    a detachment mechanism having an engaged mode and a disengaged mode, the detachment mechanism includes an engagement member that has an up-turned distal end portion that passes through the first open space, through the aperture and into the second open space during the engaged mode;
    the up-turned distal end portion of the engagement member has an opening therethrough, and a portion of the locking member is within said opening of the engagement member and within said second open space during the engaged mode whereby the delivery system secures the medical device; a kicker member configured for separating the implantable medical device from the tubular carrier member, wherein the kicker member comprises a first end and a second end, the first and second ends being embedded within the distal end of the tubular carrier member; and
    a proximal portion of the locking member is fixedly secured to the proximal portion of the carrier member and is fixedly secured to the carrier member proximal portion separated upon breaking of the frangible portion, whereby proximal axial movement of said locking member proximal portion within the lumen results in the disengaged mode and retracts the locking member from the opening of the engagement member of the detachment mechanism and thus disengages the proximal end of the implantable medical device from the delivery system to deliver same to a target location of a body vessel.

2. The delivery system of claim 1, wherein said two notches are substantially identical to each other.

3. The delivery system of claim 1, wherein said carrier member is substantially comprised of a metallic material.

4. A method of deploying an implantable medical device to a target location of a body vessel, comprising:
    providing a delivery system having (a) a generally hollow tubular carrier member defining a longitudinal axis and having a wall thickness, a lumen, a circumference, a distal portion, a proximal portion, and a frangible portion intermediate the distal portion and the proximal portion, the frangible portion being a bi-directional break hinge having two notches passing entirely through the wall thickness along an arcuate extent less than the circumference; (b) a locking member tube or wire at least partially received within the carrier member lumen, extending at least from the proximal portion of the carrier member to the distal portion of the carrier member, and having a proximal portion fixedly secured to the proximal portion of the carrier member; (c) a detachment mechanism having an engaged mode and a disengaged mode, the detachment mechanism having a kicker member with first and second ends embedded within the distal end of the tubular carrier member and an engagement member with an up-turned distal end portion having an opening therethrough; and (d) an implantable medical device having a proximally extending member at a proximal end thereof, the proximally extending member having oppositely facing first and second faces and an aperture through same and through the faces, the faces being spaced away from the carrier member lumen thereby defining first and second open spaces, the implantable medical device being mechanically and releasably connected to the detachment mechanism at or adjacent to the distal portion of the carrier member;

imparting the engaged mode whereby the up-turned distal end portion is passed through the first open space, through the aperture of the implantable medical device and into the second open space, whereby a portion of the locking member is within the opening of the engagement member and within the second open space;

positioning the implantable medical device generally adjacent to a target location of a body vessel, with the frangible portion remaining outside of the body vessel;

breaking the carrier member at the frangible portion by applying a human digital breaking force and bending the frangible portion about the break hinge, said bending being generally transverse to the longitudinal axis of the carrier member and having a breaking strength less than a breaking strength about any other line transverse to said longitudinal axis, thereby providing a separated carrier member proximal portion;

proximally moving the separated carrier member proximal portion away from the distal portion of the carrier member to longitudinally move the locking member within the carrier member lumen and out of the opening of the engagement member; and imparting the disengaged mode by mechanically retracting the locking member from the engagement member opening and disengaging the engagement member up-turned distal end portion from the proximal end aperture of the implantable medical device allowing moving of the kicker member and deploying the implantable medical device to a target location of a body vessel.

5. The method of claim 4, wherein said moving the proximal portion of the carrier member away from the distal portion of the carrier member includes moving the proximal portion of the carrier member away from the distal portion of the carrier member along a path substantially parallel to the longitudinal axis of the carrier member.

6. The method of claim 4, wherein said moving the proximal portion of the carrier member away from the distal portion of the carrier member includes moving the proximal portion of the carrier member away from the distal portion of the carrier member along a path at an angle to the longitudinal axis of the carrier member.

7. The method of claim 4, further comprising providing an introducer having a lumen and a distal end and positioning said distal end of the introducer generally adjacent to the target location of the body vessel, wherein said positioning the implantable medical device includes moving the implantable medical device through said lumen of the introducer to said distal end of the introducer.

8. The method of claim 4, further comprising providing an introducer having a lumen and a distal end and positioning at least a portion of the implantable medical device within the lumen at or adjacent to said distal end of the introducer, wherein said positioning the implantable medical device includes positioning the distal end of the introducer and the implantable medical device generally adjacent to the target location of the body vessel.

9. The method of claim 4, wherein said applying a human digital breaking force is in the direction of a notch.

10. The method of claim 4, wherein said applying a human digital breaking force is in the direction opposite a notch.

* * * * *